(12) United States Patent
Bückle

(10) Patent No.: US 9,566,382 B2
(45) Date of Patent: Feb. 14, 2017

(54) BOTTLE SUPPORT FOR AN INJECTION OR INFUSION DEVICE

(71) Applicant: Ulrich GmbH & Co. KG, Ulm (DE)

(72) Inventor: Norbert Bückle, Bernstadt (DE)

(73) Assignee: ULRICH GMBH & CO. KG, Ulm (DE)

(*) Notice: Subject to any disclaimer, the term of this patent is extended or adjusted under 35 U.S.C. 154(b) by 0 days.

(21) Appl. No.: 14/732,913

(22) Filed: Jun. 8, 2015

(65) Prior Publication Data

US 2015/0359961 A1    Dec. 17, 2015

(30) Foreign Application Priority Data

Jun. 16, 2014 (DE) ........................ 10 2014 108 452

(51) Int. Cl.
*A61M 5/14* (2006.01)
*A61J 1/16* (2006.01)
*F16B 2/12* (2006.01)
*A61J 1/05* (2006.01)

(52) U.S. Cl.
CPC .............. *A61M 5/1415* (2013.01); *A61J 1/16* (2013.01); *F16B 2/12* (2013.01); *A61J 1/05* (2013.01)

(58) Field of Classification Search
CPC .............. A61J 9/06; A61J 9/0623; A61J 1/16; A61J 1/05; A61M 5/1415; A61M 5/1417; A61M 5/1414; F16B 2/12; B01L 2200/023; B01L 9/50; A47G 23/0241; B67D 3/0032; B67D 3/0035; B60N 3/106
USPC ................... 248/311.3, 231.21, 231.85, 312, 313,248/229.26, 229.12, 229.22, 228.3, 230.3,248/231.41
See application file for complete search history.

(56) References Cited

U.S. PATENT DOCUMENTS

| | | | | |
|---|---|---|---|---|
| 1,643,661 A | * | 9/1927 | Kendall | A47J 43/287 211/65 |
| 1,688,148 A | * | 10/1928 | Martin | B60Q 7/00 211/86.01 |
| 2,196,356 A | * | 4/1940 | De Sipio | A47K 5/10 222/130 |
| 5,582,377 A | * | 12/1996 | Quesada | A47F 5/083 24/343 |
| 6,070,761 A | | 6/2000 | Bloom et al. | |

(Continued)

FOREIGN PATENT DOCUMENTS

| | | |
|---|---|---|
| DE | 4124563 A1 | 1/1993 |
| DE | 202010000281 U1 | 9/2011 |
| DE | 102011018909 A1 | 12/2011 |

OTHER PUBLICATIONS

Result of Examination Report for German Patent Application No. 10 2014 108 452.7 filed Jun. 16, 2014.

*Primary Examiner* — Anita M King
(74) *Attorney, Agent, or Firm* — Paul D. Bianco; Fleit Gibbons Gutman Bongini & Bianco PL

(57) ABSTRACT

A bottle support for an injection or infusion device with a main body, which has at least one bottle holder for the holding of a neck of a supply bottle. In order to bring about as simple and quick an equipping as possible of the injection device with supply bottles with different sizes and to hold the supply bottles securely in the bottle support, provision is made so that a shaft is formed in the main body, in which a tension slide, pretensioned with a spring, is supported so it can be displaced linearly. In a first position, the tension slide locks the neck of the supply bottle, and in a second position, the neck of the supply bottle is released.

16 Claims, 2 Drawing Sheets

(56) References Cited

U.S. PATENT DOCUMENTS

| | | | | |
|---|---|---|---|---|
| 6,394,285 B1* | 5/2002 | Arthurs | ............... | A47L 15/505 |
| | | | | 211/41.9 |
| 6,837,472 B1* | 1/2005 | Beutz | ..................... | A45F 3/16 |
| | | | | 224/148.4 |
| 7,621,495 B2* | 11/2009 | Young | ..................... | B01L 9/50 |
| | | | | 24/326 |
| 7,866,617 B2* | 1/2011 | Kleitsch | ............. | A61M 5/1417 |
| | | | | 248/228.5 |
| 8,550,413 B2 | 10/2013 | Warrick et al. | | |
| 2005/0275229 A1* | 12/2005 | Cvijic | ..................... | A61J 9/06 |
| | | | | 294/210 |
| 2011/0266409 A1 | 11/2011 | Warrick et al. | | |
| 2014/0026388 A1 | 1/2014 | Warrick et al. | | |

* cited by examiner

BOTTLE SUPPORT FOR AN INJECTION OR INFUSION DEVICE

FIELD OF THE INVENTION

The invention concerns a bottle support of an injection or infusion device.

BACKGROUND

From the state of the art, injection devices are known, which are used in the area of medical technology for the injection of liquids into the body of a patient. Such injection devices can, for example, be used to administer contrast agents during the carrying out of imaging processes, such as computer tomography, ultrasound investigations, and magnetic resonance imaging (MRI). The liquids to be injected, such as various contrast agents and NaCl rinse solutions, are thereby poured into supply bottles. The bottles with the liquids to be injected are, for example, suspended on the upper end of a rack, which is, as a rule, mounted on roller bearings, or they are supported in a bottle support with a bottle holder and connected with an injection device via a supply tube.

Such a device is known from U.S. Pat. No. 6,070,761 A. This has several bottle supports for supply bottles, wherein each bottle support is composed of two outer arms and two inner arms. The outer arms are rigidly placed on a panel and have an arch-shaped bottle holder to hold the head or neck of a supply bottle. In the outer arms, the inner arms with a likewise arch-shaped bottle holder to hold the neck of the supply bottle are supported in such a way that they can swivel. In order to be able to hold supply bottles of various sizes, the bottle holders of the outer and the inner arms differ in their diameter. To hold the larger supply bottle, the neck of the bottle of the large supply bottle, which is introduced headfirst, is inserted into the holding section of the outer arms. The inner arms are thereby swiveled out from the outer arms. To hold a smaller supply bottle, the inner arms are swiveled into the outer arms, wherein the neck of the small supply bottle, introduced headfirst, is inserted in the bottle holder of the inner arms. The two different diameters of the bottle holders of the outer and inner holding arms allow two supply bottles of different sizes to be held.

The non-variable diameters of the bottle holders of the outer and inner arms permit only the use of two supply bottles of a certain size. It is therefore not possible to use smaller or larger supply bottles with diameters that deviate from this.

Another disadvantage of the known bottle holder is found when using the outer and inner arms. Thus, when inserting a large supply bottle into the bottle holder of the outer arms unintentionally, the inner arms cannot swivel into the outer arms, since they are not reliably held in the swiveled-out position and thus the insertion of the large supply bottle is additionally complicated.

Moreover, the neck of the supply bottle is not fixed in the bottle holder, but rather is only inserted in the bottle holder.

SUMMARY OF THE INVENTION

The disclosure includes a bottle support for an injection or infusion device that allows an equipping of the injection device with supply bottles of different sizes that is as simple and rapid as possible, and the supply bottles can be held securely in the bottle support.

Other embodiments are also disclosed.

The bottle support in accordance with the invention for an injection or infusion device comprises a main body, which has at least one bottle holder for holding a neck of a supply bottle, wherein a shaft is formed in the main body, in which a tension slide, pretensioned with a spring, is supported so it can be displaced linearly, which locks in a first position of the neck of the supply bottle, and releases the neck of the bottle in a second position. By using a tension slide, it is possible to hold and lock, securely and quickly, supply bottles of different sizes in the bottle holder.

In a particularly advantageous development, the tension slide has at least one projection, which protrudes into the bottle holder in the first position and does not engage with the bottle holder in the second position, or does not protrude into it.

In another appropriate embodiment, the bottle support has a locking mechanism, which fixes the tension slide in the first position. The locking mechanism appropriately comprises an elastic lug on the tension slide and a stop surface on a wall of the shaft. The locking mechanism fixes the tension slide in the first position in the shaft in that the elastic lug locks in on the stop surface and, in this way, limits the linear displacement of the tension slide, pretensioned by the spring. The arrangement of the lug and the corresponding stop surface can also be conversely designed.

The tension slide can be appropriately brought into the second position by an external pressure on the tension slide against the resetting force of the spring. The external pressure can be applied manually by an operator of the device. In an appropriate embodiment, a handle is provided on the main body, which serves as a counter-pressure bearing by manually pushing the tension slide into the recess.

In a preferred development, the main body has a first and a second arm, both of which are designed to be rigid. Alternatively, however, the arms can also be easily made to be elastic, relative to one another. With a pushing in or insertion of the neck of the supply bottle, the two arms, as a result of the spring effect, are pressed apart and hold the neck of the bottle, in addition to the tension slide. Thus, production inaccuracies with the supply bottle, such as a wider neck of the bottle, can be balanced out.

In another advantageous embodiment, the bottle support has a second bottle holder, which is appropriately designed, like the first bottle holder, as a recess, in particular, as a borehole, in the main body. The second bottle holder allows other supply bottles of different sizes, in particular smaller supply bottles, to be held.

BRIEF DESCRIPTION OF THE DRAWINGS

These and other advantages of the bottle support in accordance with the invention for an injection or infusion device can be deduced from the embodiment example, described below in more detail, with reference to the accompanying drawing. The figures show the following.

DETAILED DESCRIPTION OF PREFERRED EMBODIMENTS

Figure 1:
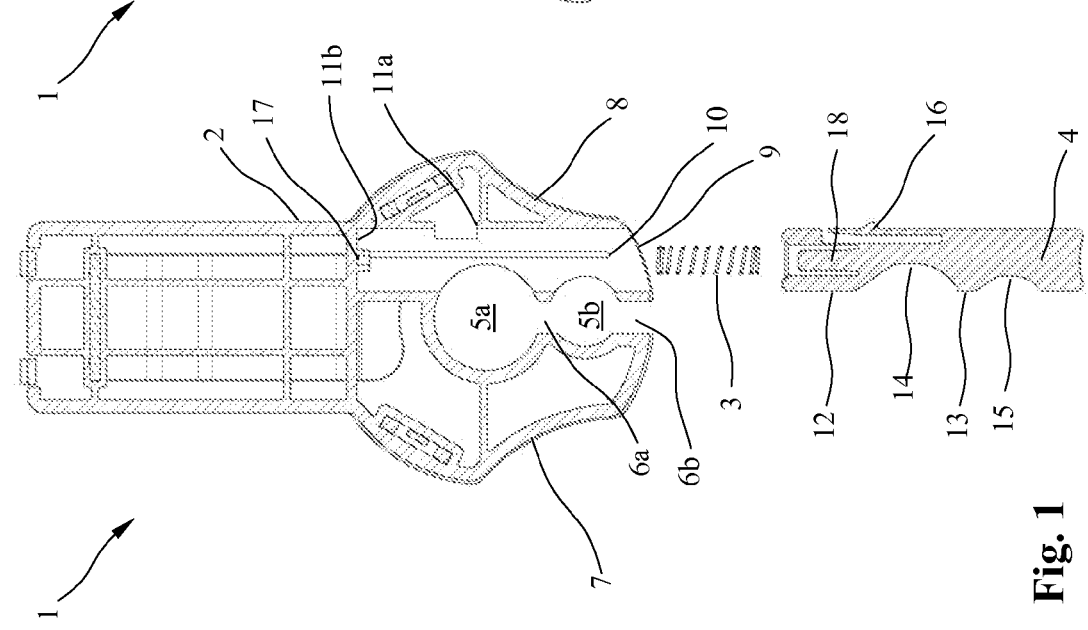
FIG. 1, a sectional representation of an exploded view of a bottle support in accordance with the invention.

FIG. 1 shows an exploded view of a bottle support 1 in accordance with the invention for an injection or infusion device with a main body 2, a spring 3, and a tension slide 4. For the holding of a neck of a bottle of a supply bottle V (shown in FIG. 4), the main body 2 has a first bottle holder 5a and a second bottle holder 5b, which are made as a recess, in particular, as a borehole in the main body 2. The diameter of the first bottle holder 5a is greater than the diameter of the second bottle holder 5b. The neck of a supply bottle V can be inserted, headfirst, into the first and second bottle holders 5a, 5b.

A channel 6a extends between the recesses of the bottle holders 5a, 5b. In addition, another channel 6b is provided, which extends outward from the bottle holder 5b through the main body 2. By means of the channels 6a, 6b and the bottle holders 5a, 5b, the main body 2 exhibits a tongs-like development in the form of a first arm 7 and a second arm 8. The arms 7, 8 are made to be slightly elastic and flexible relative to one another. The bottle holders 5a, 5b and the channels 6a, 6b are thereby in a row, as can be seen from FIGS. 1 and 2.

As a result of the channels 6a, 6b, a supply bottle V, already connected with a supply tube (which is not depicted), can be introduced laterally into the bottle support 1 and inserted into the bottle holder 5a or 5b. The channels 6a, 6b are therefore used for conducting through the supply tube.

A linear shaft 9 is formed in the shape of a recess in the main body 2 in the area of the second arm 8. The shaft 9 hereby intersects the border areas of the bottle holders 5a, 5b and is at least partially opened toward them. Furthermore, a guide bar 10 is located in the shaft 9 on an outer wall, in particular, in the bottom; it extends, more or less, over the complete length of the shaft 9. In the shaft 9, moreover, a lateral first stop surface 11a and a front second stop surface 11b are provided.

On its underside (not depicted), the tension slide 4 has a groove corresponding to the guide bar 10. Laterally, a first projection 12 and a second projection 13 are formed on the tension slide 4, wherein a first indentation 14 and a second indentation 15 follow the projections 12, 13. An elastic lug 16 is formed on a side of the tension slide 4, opposite the projections 12, 13. The stop surface 11a and the elastic lug 16 together form a locking mechanism, which is explained more precisely in the following figures.

For the assembly of the bottle support 1, the spring 3 is first pushed into or inserted into the shaft 9, wherein a holder pin 17 to hold the spring 3 is formed on the opposite shaft wall. Subsequently, the tension slide 4 is pushed into the shaft 9, so that the guide bar 10 runs in the groove of the tension slide 4 and guides it reliably in the shaft 9. Also, on the tension slide 4, a spring holder in the shape of a pin 18, via which an end area of the spring 3 is conducted, is provided.

Figure 2A:
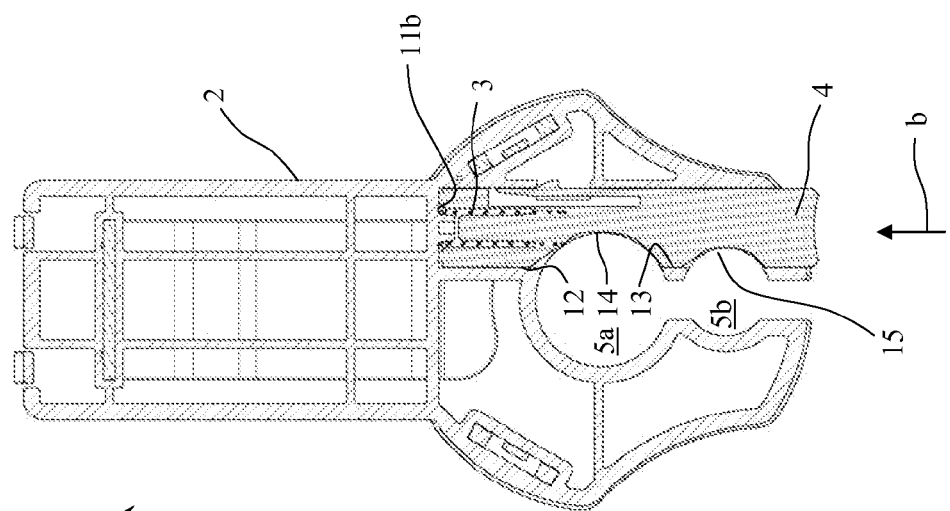
FIG. 2a, a sectional representation of the bottle support in accordance with the invention of FIG. 1 in a first position.
Figure 2B:
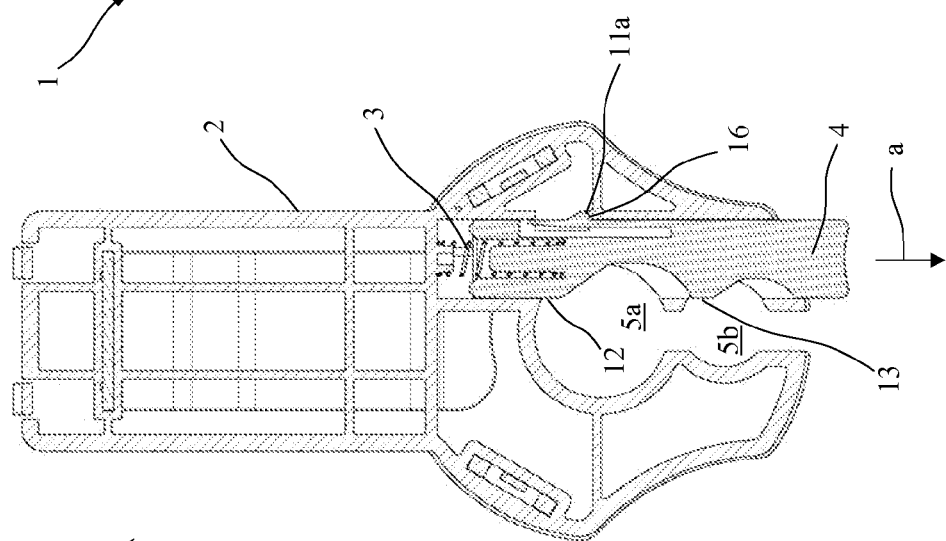
FIG. 2b, a sectional representation of the bottle support in accordance with the invention of FIG. 1 in a second position.

In the sectional representations of FIG. 2, the assembled bottle support, as previously described, with the spring 3 inserted into the main body 2 of the bottle support 1 and the tension slide 4 is shown in a first position (FIG. 2a) and in a second position (FIG. 2b).

In the first position, shown in FIG. 2a, the tension slide 4, pushed into the shaft 9, is pressed out or displaced from the shaft 9 in the direction of the arrow as a result of the spring 3. For the fixing of the tension slide 4, the locking mechanism is provided; it fixes the tension slide 4 in the first position in that the elastic lug 16 of the tension slide 4 is locked in on the stop surface 11a and thus limits the linear displacement of the tension slide 4, pretensioned by the spring 3. In the first position of the tension slide 4, the first projection 12 protrudes into the bottle holder 5a and the second projection 13 protrudes into the bottle holder 5b. A neck of a supply bottle V, inserted into the bottle holder 5a or 5b, is thus locked in the bottle holder 5a or 5b by the clamping effect of the projection 12 or 13 of the tension slide 4 engaging in the individual bottle holder 5a or 5b.

As alluded to in FIG. 2b, the tension slide 4 can be brought into the second position by an external pressure on the tension slide 4 in the direction of the arrow b, against the resetting force of the spring 3. The linear displacement of the tension slide 4 into the shaft 9, against the resetting force of the spring 3, is thereby limited by the front second stop surface 11b of the shaft 9. The shape of the indentation 14 on the tension slide 4 is thereby adapted to the shape of the first bottle holder 5a, and the shape of the indentation 15 is adapted to the shape of the second bottle holder 5b. With the depicted circular recess, the shape of the indentation is circular-segmented. As a result of this development of the indentations 14, 15 of the tension slide 4, the neck of the supply bottle V can be inserted into one of the bottle holders 5a, 5b in the second position of the tension slide 4, or a neck of the supply bottle V locked in the bottle holder 5a, 5b can be released. The projections 12 and 13, provided for the locking of the neck of the supply bottle V, thus do not engage with one of the bottle holders 5a, 5b in the second position in the shaft 9.

As can be seen from the description of the first and the second positions of the tension slide 4, the tension slide 4 is always pressed by the spring 3 into the first position, that is, the locking position. The elastic locking lug 16 is hereby used as a stop, so that the tension slide 4 does not fall out or get pressed out of the shaft 9. In the second position, that is, the release position, the tension slide 4 holds on merely by the operator holding firm or by clamping on the neck of the supply bottle 4 [sic; V].

Figure 3:
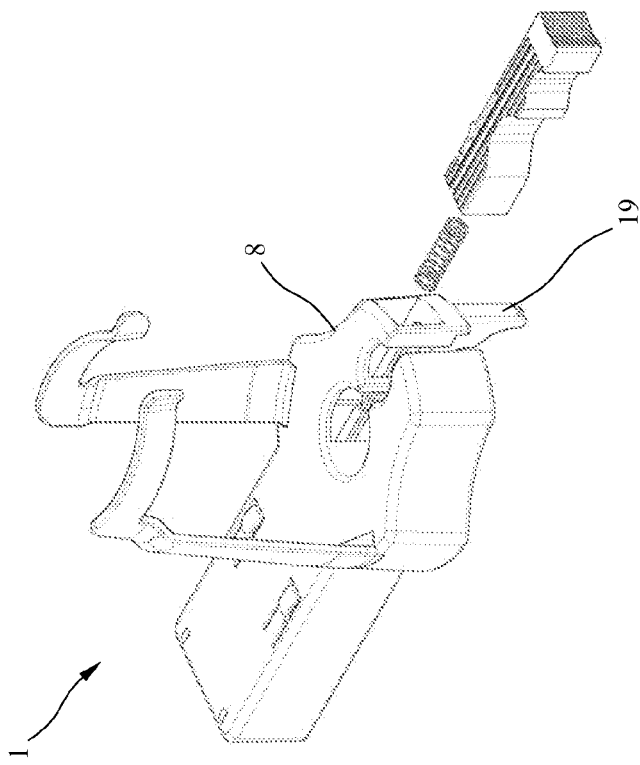
FIG. 3, a perspective representation of the exploded view of a bottle support in accordance with the invention with a counter-pressure bearing.

For the one-hand operation of the bottle support 1, a handle 19, shown in FIG. 3, which is located on the second arm 8 of the main body 2, is provided. The handle 19 is used as a counter-pressure bearing during the manual pushing in of the tension slide 4 into the shaft 9.

In the representations of FIG. 4, the use of supply bottles V, V' of different sizes can be seen. Thus, in the second bottle holder 5b, small supply bottles V' with a filling capacity of, for example, 20 mL (FIG. 4a) can be held, whereas in the first bottle holder 5a, supply bottles V with a filling capacity of, for example, 100 mL (FIG. 4b), 500 mL (FIGS. 4c), and 1000 mL (FIG. 4d) can be inserted.

Figure 4A:
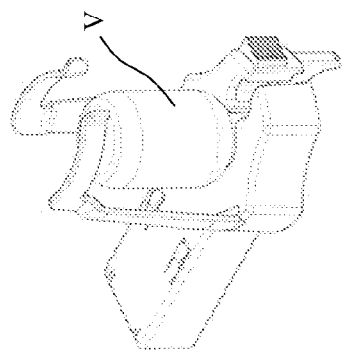
FIG. 4a, a perspective representation of the bottle support in accordance with the invention of FIG. 3 with a 20-mL supply bottle.
Figure 4B:
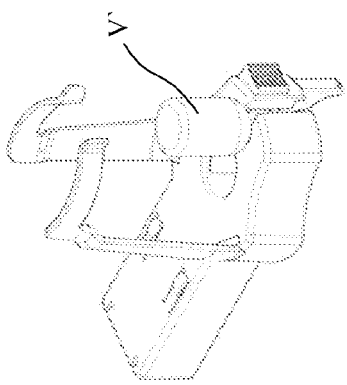
FIG. 4b, a perspective representation of the bottle support in accordance with the invention of FIG. 3 with a 100-mL supply bottle.
Figure 4C:
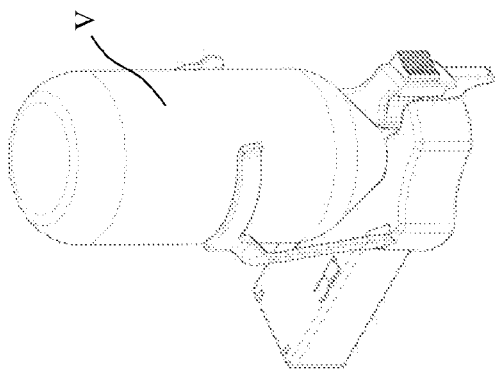
FIG. 4c, a perspective representation of the bottle support in accordance with the invention of FIG. 3 with a 500-mL supply bottle.
Figure 4D:
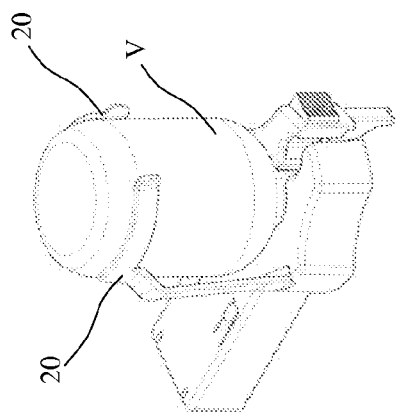
FIG. 4d, a perspective representation of the bottle support in accordance with the invention of FIG. 3 with a 1000-mL supply bottle.

In order to additionally secure the supply bottle V held in the first bottle holder 5a, as can be seen from the FIGS. 4c and 4d, flexible holding elements 20 are located on the main body 2 or the first and second arms 7, 8 of the bottle support 1; on their outer circumference, they embrace, at least partially, and in a force-locking and/or form-locking manner, the supply bottle V that is held in the bottle holder 5a.

The invention is not limited to the embodiment example described. Thus, the bottle support in accordance with the invention can be used not only in an injection device for the injection of contrast agents, but also, for example, in infusion devices. In contrast to the described embodiment example, only one bottle holder or even more bottle holders can be provided in the main body instead of a first and second bottle holder 5a, 5b, depending on the application case. It is also possible to use a bottle support in accordance with the invention for the holding of a supply bottle together with a traditional bag support for the holding of a bag containing a liquid to be injected.

The bottle holder 1 is, moreover, not limited to the holding of supply bottles with the previously described filling capacities.

The invention claimed is:

1. A bottle support for an injection or infusion device, the bottle support comprising:
    a main body, which has at least one bottle holder configured to hold a neck of a supply bottle,
    a shaft formed in the main body,
    a tension slide, pretensioned with a spring, supported in such a way that the tension slide can be displaced linearly in the shaft, and, in a first position, the tension slide locks the neck of the supply bottle, while in a second position, the tension slide releases the neck of the bottle,
    wherein the tension slide has at least one projection, which, in the first position, protrudes into the at least one bottle holder and, in the second position, does not protrude into the at least one bottle holder, and
    wherein the at least one bottle holder is formed as a borehole in the main body.

2. The bottle support according to claim 1, wherein a locking mechanism fixes the tension slide in the first position.

3. The bottle support according to claim 2, wherein the locking mechanism comprises an elastic lug on the tension slide and a stop surface on a wall of the shaft.

4. A bottle support for an injection or infusion device, the bottle support comprising:
    a main body, which has at least one bottle holder configured to hold a neck of a supply bottle,
    a shaft formed in the main body,
    a tension slide, pretensioned with a spring, supported in such a way that the tension slide can be displaced linearly in the shaft, and, in a first position, the tension slide locks the neck of the supply bottle, while in a second position, the tension slide releases the neck of the bottle,
    a locking mechanism fixing the tension slide in the first position, the locking mechanism comprising an elastic lug on the tension slide and a stop surface on a wall of the shaft.

5. The bottle support according to claim 4, wherein the tension slide has at least one projection, which, in the first position, protrudes into the at least one bottle holder and, in the second position, does not protrude into the at least one bottle holder.

6. The bottle support according to claim 5, wherein the locking mechanism fixes the tension slide in the first position in the shaft, the elastic lug locks in on the stop surface and, in this way, limits the linear displacement of the tension slide, pretensioned by the spring.

7. The bottle support according to claim 5, wherein the tension slide can be brought into the second position by an external pressure on the tension slide against the resetting force of the spring.

8. The bottle support according to claim 5, wherein the tension slide has at least one indentation, which has a shape adapted to the shape of the at least one bottle holder.

9. The bottle support according to claim 5, wherein the main body has a first and second arm.

10. The bottle support according to claim 5, wherein a handle, which serves as a counter-pressure bearing when the tension slide is shoved into the shaft, is provided on the main body.

11. The bottle support according to claim 5, wherein the at least one bottle support comprises a first bottle holder and a second bottle holder.

12. The bottle support according to claim 11, wherein the tension slide has a second indentation, which has a shape that is adapted to the shape of the second bottle holder.

13. The bottle support according to claim 5, wherein the shaft is formed as a recess in the main body.

14. The bottle support according to claim 5, wherein the at least one bottle holder is formed as a recess in the main body.

15. The bottle support according to claim 5, wherein a guide bar, which engages in the tension slide, is designed in the shaft.

16. A bottle support for an injection or infusion device, the bottle support comprising:
    a main body, which has a first bottle holder configured to hold a neck of a first supply bottle and a second bottle holder configured to hold a neck of a second supply bottle,
    a shaft formed in the main body,
    a tension slide having a first indentation with a shape adapted to the shape of the first bottle holder and a second indentation with a shape adapted to the shape of the second bottle holder, the tension slide pretensioned with a spring, supported in such a way that the tension slide can be displaced linearly in the shaft, and, in a first position, the tension slide locks the neck of the first supply bottle, while in a second position, the tension slide releases the neck of the first supply bottle.

* * * * *